United States Patent [19]

Abraham et al.

[11] Patent Number: 5,382,680

[45] Date of Patent: Jan. 17, 1995

[54] ALLOSTERIC HEMOGLOBIN MODIFIER COMPOUNDS

[75] Inventors: Donald J. Abraham, Midlothian, Va.; Ahmed Mehanna, Winchester, Mass.; Ramnarayan Randad, Richmond, Va.

[73] Assignee: The Center for Innovative Technology, Herndon, Va.

[21] Appl. No.: 722,382

[22] Filed: Jun. 26, 1991

Related U.S. Application Data

[63] Continuation of Ser. No. 623,346, Dec. 7, 1990, abandoned.

[51] Int. Cl.$^6$ .................................. C01C 229/34
[52] U.S. Cl. ................................... 562/451; 560/42
[58] Field of Search ..................... 560/42; 562/451

[56] References Cited

U.S. PATENT DOCUMENTS

| | | | |
|---|---|---|---|
| 4,482,571 | 11/1984 | Abraham | 424/317 |
| 4,699,926 | 10/1987 | Abraham et al. | 514/563 |
| 4,704,402 | 11/1987 | Abraham et al. | 514/543 |
| 4,731,381 | 3/1988 | Abraham et al. | 514/571 |
| 4,731,473 | 3/1988 | Abraham et al. | 562/464 |
| 4,751,244 | 6/1988 | Abraham et al. | 514/563 |
| 4,887,995 | 12/1989 | Abraham et al. | 604/4 |

FOREIGN PATENT DOCUMENTS

WO8810113 12/1988 WIPO.
WO8912622 12/1989 WIPO.

OTHER PUBLICATIONS

"Mechanisms of Cooperativity and Allosteric Regulation In Proteins", Quarterly Review of Biophysics, 22:2 (1989), pp. 139, 163 and 164, Perutz.

"LR16, a compound with potent effects on the oxygen affinity of hemoglobin, on blood cholesterol, and on low density lipoprotein", Proc. Natl. Acad. Sci. (USA) 85 (1988), pp. 6117–6121; Lalezarie et al.

Chemical Abstracts, 25-Noncondensed Aromatics, vol. 79 (1973), p. 427, No. 18434k which identifies German Patent 2,149,070.

"Allosteric modifiers of hemoglobin", Abstract #71 in American Chemical Society Division of Medicinal Chemistry, 200th ACS National Meeting, Aug. 26–31, 1990, Randad et al. (1990).

"Bezafibrate Lowers Oxygen Affinity of Hemoglobin", The Lancet, Oct. 15, 1983, pp. 881–882; Perutz (1983).

"Hemoglobin as a Receptor of Drugs and Peptides: X-ray Studies of the Stereochemistry of Binding", J. Amer. Chem. S., vol. 108, (1986), pp. 1064–1078; Perutz et al.

"Design, Synthesis, and Testing of Potential Antisickling Agents. 4. Structure–Activity Relationships of Benzyloxy and Phenoxy Acids", J. Med. Chem., vol. 27, (1984), pp. 967–978; Abraham et al.

(List continued on next page.)

Primary Examiner—José G. Dees
Assistant Examiner—B. Frazier
Attorney, Agent, or Firm—Whitham, Curtis, Whitham & McGinn

[57] ABSTRACT

Allosteric hemoglobin modifier compounds having the general structural formula:

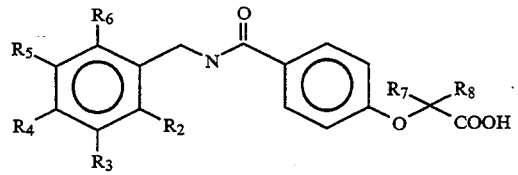

wherein the $R_2$, $R_3$, $R_4$, $R_5$, and $R_6$ moieties may be hydrogen, halogen or alkyl groups and may be the same or different, and wherein the $R_7$ and $R_8$ moieties may be hydrogen or methyl groups and may be the same or different.

2 Claims, 1 Drawing Sheet

OTHER PUBLICATIONS

"Design, Synthesis, and Testing of Potential Antisickling Agents. 7. Ethacrynic Acid Analogues", J. Med. Chem., vol. 32, (1989), pp. 2460–2467; Abraham et al.

"Standardization of Hemoglobinometry. 1. The Extinction Coefficient of Hemiglobincyanide", Clinica Chimica Acta, vol. 5, (1960), pp. 719–726; Zijlstra et al.

"Spectrophotometry of Haemoglobin: The Standard Haemiglobin Cyanide Method and After", J. Clin. Chem. Biochem., vol. 19, (1981), pp. 521–523; Zijlstra et al.

"Studies on the Heterogeneity of Hemoglobin. XIII. Chromotagraphy of Various Human and Animal Hemoglobin Types of DEAE-Sephadex", J. Chrom., vol. 32, (1968), pp. 723–727; Dozy et al.

Hemoglobin Structure/Function, lecture by Dr. Abraham on Oct. 3, 1990.

4-chlorobenzylamine   p-hydroxybenzoicacid   4-(4-chlorobenzyl)-4-hydroxy-benzamide 2(4-(((4-chlorobenzyl)amino)carbonyl)phenoxy)-2-methylproprionic acid

ALLOSTERIC HEMOGLOBIN MODIFIER COMPOUNDS

This is a continuation of U.S. application Ser. No. 07/623,346, filed Dec. 7, 1990, now abandoned.

CROSS-REFERENCE TO RELATED APPLICATIONS

This patent application is related to the copending patent application entitled "ALLOSTERIC HEMOGLOBIN MODIFIERS" which was filed on Feb. 12, 1990, and has Ser. No. 07/478,848, now U.S. Pat. No. 5,049,695, and that patent is herein incorporated by reference.

DESCRIPTION

BACKGROUND OF THE INVENTION

1. Field of the Invention

The subject invention is generally related to compounds which are capable of allosterically modifying hemoglobin and, more particularly, to a family of new compounds which, when mixed with blood, interact with hemoglobin to drive the allosteric equilibrium toward a low oxygen affinity state.

2. Description of the Prior Art

Hemoglobin is a tetrameric protein which delivers oxygen via an allosteric mechanism. Oxygen binds to the four hemes of the hemoglobin molecule. Each heme contains porphyrin and iron in the ferrous state. The ferrous iron-oxygen bond is readily reversible. The first oxygen bound to a heme requires much greater energy than the second oxygen molecule, binding the third oxygen requires even less energy, and the fourth oxygen requires the lowest energy for binding. Hemoglobin has two $\alpha$ and two $\beta$ subunits-arranged with a two fold symmetry. The $\alpha$ and $\beta$ dimers rotate during oxygen release to open a large central water cavity. The allosteric transition that involves the movement of the alpha-beta dimer takes place between the binding of the third and fourth oxygen. The $\alpha_1\beta_1$ interface binding is tighter than the $\alpha_1\alpha_2$ or $\alpha_1\beta_2$ interfaces.

In blood, hemoglobin is in equilibrium between two allosteric structures. In the "T" (for tense) state, hemoglobin is deoxygenated. In the "R" (for relaxed) state, hemoglobin is oxygenated. An oxygen equilibrium curve can be scanned, using well known equipment such as the AMINCO ™ HEM-O-SCAN, to observe the affinity and degree of cooperativity (allosteric action) of hemoglobin. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined (i.e., this is the pressure in mm Hg when the scanned hemoglobin sample is 50% saturated with oxygen). Under physiological conditions (i.e., 37° C., pH=7.4, and partial carbon dioxide pressure of 40 mm Hg), the $P_{50}$ value for normal adult hemoglobin (HbA) is around 26 mm Hg. If a lower than normal $P_{50}$ value is obtained for the hemoglobin under test, the scanned curve is considered to be "left-shifted" and the presence of high affinity hemoglobin is indicated. Conversely, if a higher than normal $P_{50}$ value is obtained for the hemoglobin under test, the scanned curve is considered to be "right-shifted" and the presence of low affinity hemoglobin is indicated.

It has been proposed that influencing the allosteric equilibrium of hemoglobin is a viable avenue of attack for treating diseases. The conversion of hemoglobin to a high affinity state is generally regarded to be beneficial in resolving problems with deoxy Hemoglobin-S (sickle cell anemia). The conversion of hemoglobin to a low affinity state is believed to have general utility in a variety of disease states where tissues suffer from low oxygen tension, such as ischemia and cancer. Several synthetic compounds have been identified which have utility in the allosteric regulation of hemoglobin and other proteins. For example, several new compounds and methods for treating sickle cell anemia which involve the allosteric regulation of hemoglobin are reported in U.S. Pat. No. 4,482,571 to Abraham, U.S. Pat. No. 4,699,926 to Abraham et al., U.S. Pat. No. 4,731,381 to Abraham et al., U.S. Pat. No. 4,731,473 to Abraham et al., U.S. Pat. No. 4,751,244 to Abraham et al., and U.S. Pat. No. 4,887,995 to Abraham et al. Furthermore, in both Perutz, "Mechanisms of Cooperativity and Allosteric Regulation in Proteins", *Quarterly Reviews of Biophysics* 22, 2 (1989), pp. 163–164, and Lalezari et al., "LR16, a compound with potent effects on the oxygen affinity of hemoglobin, on blood cholesterol, and on low density lipoprotein", *Proc. Natl. Acad. Sci., U.S.A.* 85 (1988), pp. 6117–6121, compounds which are effective allosteric hemoglobin modifiers are discussed. The structure of certain other synthetic compounds which decrease the oxygen affinity of hemoglobin is reported in the abstract by Randad et al., "Allosteric modifiers of hemoglobin. Synthesis and Testing of Novel compounds to decrease the oxygen affinity of hemoglobin" *American Chemical Society Division of Medicinal Chemistry*, Item #71, 200th ACS National Meeting, Washington D.C., Aug. 26–31, 1990; however, no data is provided with the abstract.

SUMMARY OF THE INVENTION

It is an object of this invention to provide a family of new compounds which are capable of allosterically modifying hemoglobin such that it is present in blood in a lower oxygen affinity state.

It is another object of this invention to provide a method of shifting the T-state of hemoglobin by providing a compound in the blood which is capable of allosterically modifying hemoglobin.

According to the invention, new compounds have been synthesized and their effect on the $P_{50}$ value of hemoglobin has been determined. Each of the molecules fall within a family of compounds having the general structural formula illustrated in FIG. 1 of the drawings, wherein $R_2$, $R_3$, $R_4$, $R_5$, $R_6$ may be a hydrogen, halogen or alkyl group, and $R_7$ and $R_8$ may be either hydrogen or methyl and these moieties may be the same or different. Each of the compounds was found to increase the $P_{50}$ value of hemoglobin; hence, the compounds are capable of driving the allosteric equilibrium of hemoglobin towards a condition favoring the low oxygen affinity state.

BRIEF DESCRIPTION OF THE DRAWINGS

The foregoing and other objects, aspects and advantage will be better understood from the following detailed description of the preferred embodiment of the invention with reference to the drawings, in which.

DETAILED DESCRIPTION OF THE PREFERRED EMBODIMENTS OF THE INVENTION

The present invention provides a group of organic compounds capable of shifting the hemoglobin allosteric equilibrium toward the low affinity "T" state. The low affinity "T" state will deliver more oxygen to tissues. Thus, the compounds of the invention should be valuable as antischemic agents, as sensitizers for x-ray irradiation in cancer therapy, as antilipidemic agents, in preparing blood substitutes, and in blood storage.

Figure 1:
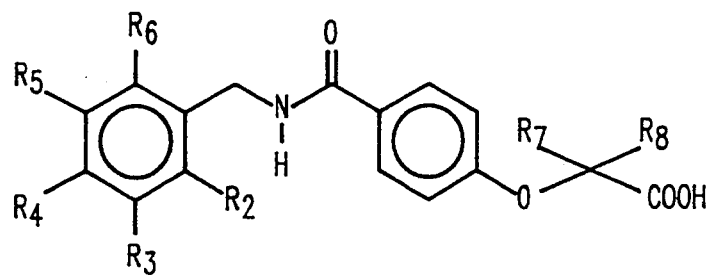
FIG. 1 illustrates the general structural formula of the new compounds which embody the principles and concepts of the invention.

FIG. 1 illustrates the general structural formula of the compounds contemplated by the present invention which are 2[4-(((benzyl) amino)carbonyl)phenoxy]-2-methyl propionic acids. The $R_2$, $R_3$, $R_4$, $R_5$, $R_6$ moieties can be either hydrogen, halogen or alkyl groups and may be the same or different. The $R_7$ and $R_8$ moieties may preferably be either hydrogen (H) or methyl ($CH_3$) groups and also may be the same or different. Examples 1 through 4 discussed below provide the synthesis routes for several compounds which are contemplated by the present invention and, specifically, 2[4-(((4-chlorobenzyl)amino) carbonyl)phenoxy)-2-methyl propionic acid, 2[4-(((4-methylbenzyl)amino)carbonyl)-phenoxy)-2-methyl propionic acid, 2[4-(((3,4 dichlorobenzyl)amino) carbonyl)phenoxy)-2-methyl propionic acid, and 2[4-(((benzyl)amino)carbonyl)-phenoxy-2-methyl propionic acid, respectively. While Examples 1 through 4 outline the synthesis for producing four compounds within the family of compounds defined by the structural formula of FIG. 1, it should be understood that other compounds within the family can easily be synthesized by changing the starting materials. All compounds within the family would have a similar mode of binding and would, therefore, all have the effect of shifting the allosteric equilibrium of hemoglobin towards favoring the low affinity "T" state.

To test the compounds of the invention for physiological activity, human blood was obtained from the Central Blood Bank, Richmond, Va. The extraction, chromatography, and characterization of isolated hemoglobin methods used by the inventors were identical to those described by Dozy and Huisman in *J. of Chromatography*, Vol 32, (1968) pp. 723 and in *The Chromatography of Hemoglobin*, H. J. Schroeder and D. H. J. Huisman, Ed. Marcel Dekker Inc. N.Y. (1980) which are herein incorporated by reference. The purity of normal hemoglobin (HbA) was determined by gel electrophoresis, using a Gelman semimicroelectrophoresis chamber. The concentration of hemoglobin was determined according to the cyanmethemoglobin method described in Zijlstra, *Clin. Chem. Acta.*, Vol 5, pp. 719–726 (1960), and Zijlstra and Van Kamper, *J. Clin. Chem. Clin. Biochem.*, Vol. 19, p. 521 (1981) which are herein incorporate by reference. All purified hemoglobin solutions were stored in liquid nitrogen. The reagents and buffers were purchased from the following sources: Fischer Scientific, Sigma Chemical Company, and Pharmacia and Research Chemicals, Inc.

Oxygen equilibrium curves were determined on an AMINCO TM HEM-O-SCAN oxygen dissociation analyzer available from Travenol Laboratories. HbA was prepared as follows: 20 ml of whole blood from a nonsmoking donor (blood bank, Richmond, Va.) was drawn into a heparinized vacutainer. The blood was immediately packed in ice (to prevent MetHb formation) and then centrifuged (10 minutes at 2500 rpm) to separate the plasma and buffy coat from the packed erythrocytes. After centrifugation was completed, the plasma and buffy coat were removed by aspiration and the cells washed three times with 0.9% NaCl containing 40 mg of ethylenediaminetetraacetic acid (EDTA) per liter and then once with 1.0% NaCl containing 40 mg of EDTA/L. The cells were lysed by the addition of one to two volumes of deionized water containing 40 mg of EDTA/L. The mixture was allowed to stand for 30 minutes with occasional mixing before being centrifuged for 2 hours at 10,000 rpms at 4° C. for two hours to remove the remaining cell stroma. The supernatant was further purified by either gel filtration With Sephadex G-25 or dialysis against pH 8.6 tris buffer (50 mM, containing 40 mg. of EDTA/L). The sodium chloride free hemoglobin solution was chromatographed on DEAE-Sephacel ion-exchange resin (Sigma) preequilibrated with Tris buffer (pH 8.6, 50 mM, containing 40 mg of EDTA/L), the HbA fraction was then eluted with pH 8.4 Tris buffer. The pure HbA fraction (identified by electrophoresis) was concentrated using a Schleicher and Schuell collodion bag apparatus (Schleicher and Schuell, Inc.) with HEPES buffer (150 mM, pH 7.4) as the exchange buffer. The hemoglobin concentration was then determined using the above-noted cyanomethemoglobin method. The hemoglobin concentration at this point was usually found to be around 35 g% or approximately 5.5 mM. Less than 5% methemoglobin was noted even after several days at 4° C.

All compounds were mixed with one equivalent of sodium bicarbonate ($NaHCO_3$), then dissolved in the HEPES buffer to give 20 mM solutions. Just prior to running the oxygen equilibrium curve, the hemoglobin and the drug were mixed in a 1:1 ratio (50 μl of hemoglobin plus 50 μl of drug) to give 2.75 mM hemoglobin with a drug concentration of 10 mM. The control was prepared by the addition of 50 ul of hemoglobin to 50 μl of the HEPES buffer. Table 1 presents the measured $P_{50}$ values for normal hemoglobin treated with the synthesized compounds discussed in Examples 1–4:

TABLE 1

| Compound | $R_3$ | $R_4$ | $P_{50}$ control | $P_{50}$ drug | Ratio |
| --- | --- | --- | --- | --- | --- |
| Ex. 1 | H | Cl | 18 | 27 | 1.5 |
| Ex. 2 | H | $CH_3$ | 19 | 28 | 1.47 |
| Ex. 3 | Cl | Cl | 18 | 28 | 1.56 |
| Ex. 4 | H | H | 19 | 22 | 1.16 |

The ratio column represents the ratio of the $P_{50}$ drug value relative to the $P_{50}$ control value calculated by dividing the $P_{50}$ drug by the $P_{50}$ control. Each hemoglobin sample treated with one of the inventive compounds had a $P_{50}$ drug value which was greater than the $P_{50}$ control, indicating that the allosteric equilibrium for hemoglobin has been shifted towards favoring the low oxygen affinity "T" state of hemoglobin by the compounds. Table 1 only shows the moieties of $R_3$ and $R_4$ for compounds having the structure shown in FIG. 1 wherein $R_2$, $R_5$, and $R_6$ are hydrogens and $R_7$ and $R_8$ are methyl groups as can be seen by referencing Examples 1-4. Because other compounds within the family defined by FIG. 1 would have a similar mode of binding, their effect on the $P_{50}$ value can be expected to be the same as for the compounds shown in Table 1. As noted above, the $P_{50}$ value for normal adult hemoglobin is 26 under physiological conditions (where the measurement is made on whole cells). Here, the $P_{50}$ control is less than 26 because the $P_{50}$ measurement is being made on hemoglobin in solution (outside the red blood cells) where the $P_{50}$ is typically lower.

Since the compounds contemplated by this invention are capable of allosterically modifying hemoglobin so that a low oxygen affinity "T" state is favored (right shifting the equilibrium curve as indicated by the $P_{50}$ ratio column in Table 1), these compounds will be useful in treating a variety of disease states in mammals including humans where tissues suffer from low oxygen tension, such as cancer and ischemia. As pointed out by Hirst et al. in *Radiat. Res.*, Vol. 112, (1987), pp. 164, decreasing the oxygen affinity of hemoglobin in circulating blood has been shown to be beneficial in the radiotherapy of tumors. The compounds may be administered to patients in whom the affinity of hemoglobin for oxygen is abnormally high. Particular conditions include certain hemoglobinopathies and certain respiratory distress syndromes in new born infants aggravated by high fetal hemoglobin levels and when the availability of hemoglobin/oxygen to the tissues is decreased (e.g., in ischemic conditions such as peripheral vascular disease, coronary occlusion, or cerebral vascular accidents). The compounds may also be used to inhibit platelet aggregation and may be used for antithrombotic purposes. The compounds of the present invention can be added to whole blood or packed cells in order to facilitate the dissociation of oxygen from hemoglobin and improve the oxygen delivering capability of the blood. For example, when blood is stored, the hemoglobin in blood tends to increase its affinity for oxygen by losing 2,3-diphosphoglycerate and this tendency can be countered by adding the present compounds to the stored blood to restore the oxygen delivering capabilities of the stored blood. In addition, the compounds could be administered to mammals including humans to reduce or prevent hyperlipidemia and especially to reduce the levels of total serum cholesterol, low density lipoprotein cholesterol and triglycerides.

Administration can be achieved orally, by intravenous or intraperitoneal injection, or rectally by suppository where the dose and the dosing regiment is varied according to individual sensitivity and the type of disease state being treated. In addition, the compounds can be mixed with blood external to a patient's body prior to and/or simultaneously with a transfusion. The compounds can be administered in the pure form or in a pharmaceutically acceptable formulation including suitable elixirs, binders, and the like or as pharmaceutically acceptable salts or other derivatives.

EXAMPLE 1

Figure 2:
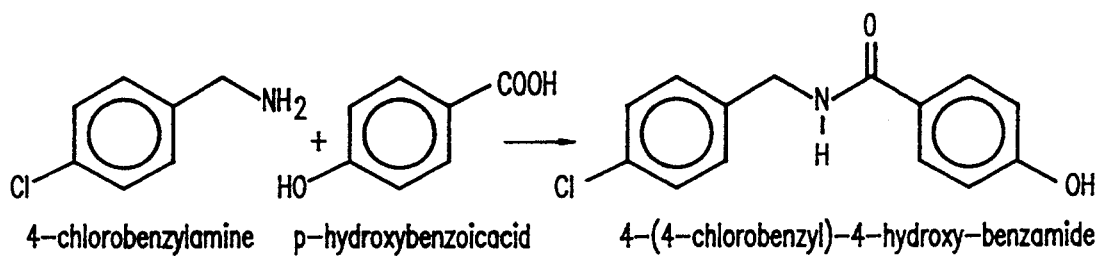
FIG. 2 illustrates the structural formulas of precursor compounds and reaction scheme for a method of synthesizing a compound as described in Example 1 which falls within the general structural formula of FIG. 1 of the drawings.
Figure 2:
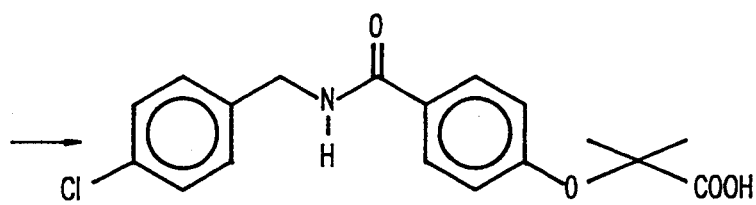

FIG. 2 illustrates a general reaction scheme for the preparation of 2(4-(((4-chlorobenzyl)amino) carbonyl)-phenoxy)-2-methyl propionic acid. In accordance with the illustrated scheme, 3.5 g (25 mmol) of p-hydroxybenzoic acid (PBA), 6.07 g (50 mmol) of 4-chlorobenzyl amine and mesitylene are added together for a total volume of 25 milliliters (ml) and this volume is heated to reflux. To this refluxing mixture is added 0.88 g (6.5 mmol) phosphorous pentachloride ($PCl_5$) and refluxing is continued for an additional hour. The cooled reaction mixture is washed with 10 ml of 1 normal (1N) hydrochloric acid (HCl) and extracted with 10 ml of 2N sodium hydroxide (NaOH). The combined alkali layer is washed with ether, then cooled and acidified with 1N HCl to provide 4.2 g of N-(4-chorobenzyl)-4-hydroxybenzamide which has the formula $C_{14}H_{12}ClNO_2$ as an intermediate product (81% yield), mp. 190°–192° C. The intermediate product is recrystallized from a 1:2 acetone:petroleum ether solution and a 1.3 g (5 mmol) portion is O-alkylated. Then 2.75 g of pulverized sodium hydroxide is added to a cooled and stirred solution of the reaction intermediate, N-(4-chlorobenzyl)-4-hydroxybenzamide, where 1.3 g (5 mmol) of N-(4-chlorobenzyl)-4-hydroxybenzamide is present in acetone for a total volume of 25 ml. Subsequently, 1.25 ml (10.4 mmol) of chloroform is added dropwise to the solution over 10 minutes. The reaction mixture is stirred overnight at room temperature and acetone is removed under vacuum. The residue is dissolved in 10 ml of water, washed with ether, and then cooled and acidified with dilute hydrochloric acid to produce a yellow precipitate of 2(4-(((4-chlorobenzyl)amino)carbonyl)-phenoxy)2-methyl propionic acid which is indicated in FIG. 2. The precipitate is purified via extraction with aqueous sodium bicarbonate followed by acidification, using dilute HCl, of the alkaline layer. The resulting propionic acid is then crystallized from a 1:2 acetone:petroleum ether mixture to produce a compound having the formula $C_{18}H_{18}ClNO_4$ in a 50% yield or 0.86 mg. The crystallized product has a melting point of 180° C.

EXAMPLE 2

The compound 2(4-(((4-methylbenzyl)amino) carbonyl)phenoxy)-2-methyl propionic acid is prepared in a manner similar to that described in Example 1. First, 3.5 g (25 mmol) of PBA, 6.05 g (50 mmol) of 4-methylbenzyl amine in mesitylene with a total volume of 25 ml are heated to reflux. To this refluxing mixture is added 0.88 g (6.5 mmol) $PCl_5$ and refluxing is continued for an additional two hours. The reaction mixture was cooled and worked up as described in Example 1 to provide N-(4-methylbenzyl)-4-hydroxybenzamide in 85% yield which has the formula $C_{15}H_{15}NO_2$ and a melting point temperature of 158°–160° C. 1.21 g (5 mmol) of the intermediate, N-(4-methylbenzyl)-4-hydroxybenzamide was O-alkylated using the procedure of Example 1 with 20 ml of acetone, 2.75 g NaOH and 1.25 ml $CHCl_3$. 0.98 g or 55% yield of the final product, 2(4-(((4-methylbenzyl) amino)carbonyl)phenoxy)-2-methyl propionic acid which has the formula $C_{19}H_{21}NO_4$, was obtained and had the melting point temperature of 172° C.

EXAMPLE 3

The procedure of Example 1 is repeated using 5.67 g (35 mmol) 3,4-dichlorobenzylamine instead of 4-chlorobenzyl amine. In this case, the intermediate product is N-(3,4-dichlorobenzyl)-4-hydroxybenzamide having formula $C_{14}H_{11}Cl_2NO_2$ and 1.48 grams (5 mmol) of the intermediate is O-alkylated with acetone (20 ml), NaOH (2.75 g) and $CHCl_3$ (1.25 ml) to produce 0.76 g (40% yield) of 2(4-(((3,4-dichlorobenzyl)amino)carbonyl)-phenoxy)-2-methyl propionic acid which has the formula $C_{18}H_{17}Cl_2NO_4$ and a melting point temperature of 148° C.

EXAMPLE 4

The procedure of Example 1 is repeated using 5.35 mg (50 mmol) of benzylamine instead of 4-chlorobenzylamine. In this case, the intermediate product is N-(benzyl)-4-hydroxybenzamide having the formula $C_{14}H_{13}NO_2$ and a melting point temperature of 160° C. 1.13 g (5 mmol) of the intermediate is O-alkylated using 20 ml of acetone, 2.75 g of NaOH, and 1.25 ml of $CHCl_3$ for twelve hours to produce 1.7 g (75% yield) of 2(4-(((benzyl)amino)carbonyl) phenoxy)-2-methyl propionic acid which has a melting point temperature of 162°–163° C.

While the invention has been described in terms of its preferred embodiment wherein a family of new compounds has been shown to drive the allosteric equilibrium of hemoglobin towards a condition favoring the low oxygen affinity state, those skilled in the art will recognize that the invention can be practiced with modification within the spirit and scope of the appended claims.

Having thus described our invention, what we claim as new and desire to secure by letters patent is the following:

1. A compound having the following structural formula:

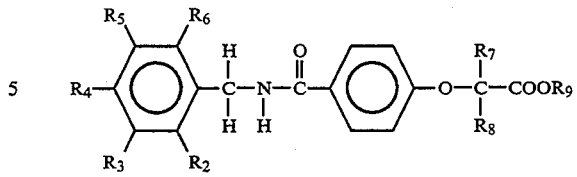

wherein the $R_2$, $R_3$, $R_4$, $R_5$, and $R_6$ moieties may be hydrogen, halogen, or alkyl groups and may be the same or different, wherein the $R_7$ and $R_8$ moieties may be hydrogen or methyl groups and may be the same or different, and wherein the $R_9$ moiety is hydrogen.

2. A compound having the following structural formula:

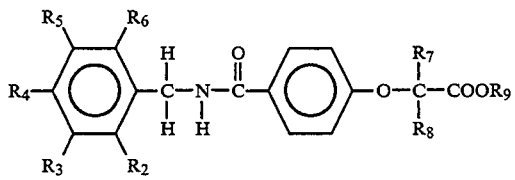

wherein the $R_2$, $R_3$, $R_4$, $R_5$, and $R_6$ moieties may be hydrogen, halogen, or alkyl groups and may be the same or different, wherein the $R_7$ and $R_8$ moieties may be hydrogen or methyl groups and may be the same or different, and wherein the $R_9$ moiety is sodium.

* * * * *